United States Patent [19]
Witt et al.

[11] Patent Number: 5,455,675
[45] Date of Patent: Oct. 3, 1995

[54] APPARATUS FOR DETERMINATION OF PARTICLE SIZES AND/OR DISTRIBUTIONS OF PARTICLE SIZES

[75] Inventors: Wolfgang Witt; Wolfgang Maus-Friedrichs; Stephan Röthele, all of Clausthal-Zellerfeld, Germany

[73] Assignee: Sympatec GmbH System-Partikel-Technik, Clausthal-Zellerfeld, Germany

[21] Appl. No.: 112,733

[22] Filed: Aug. 26, 1993

[30] Foreign Application Priority Data

Aug. 26, 1992 [DE] Germany ............... 42 28 388.4

[51] Int. Cl.⁶ ................................................ G01N 15/02
[52] U.S. Cl. ...................... 356/336; 356/338; 356/343
[58] Field of Search ........................ 356/335, 336, 356/337, 338, 343

[56] References Cited

U.S. PATENT DOCUMENTS

| | | | |
|---|---|---|---|
| 4,245,909 | 1/1981 | Loos | 356/336 |
| 4,755,052 | 7/1988 | Giglio et al. | 356/336 |
| 5,164,787 | 11/1992 | Igushi et al. | 356/336 |

Primary Examiner—Richard A. Rosenberger
Assistant Examiner—Robert Kim
Attorney, Agent, or Firm—Kenyon & Kenyon

[57] ABSTRACT

Apparatus for determination of particle sizes and/or distributions of particle sizes comprises a light source which radiates parallel light of high coherence through a measuring zone (14) in which the particles to be measured are disposed. The light beam diffracted at the particles is imaged by an imaging device (18) onto a photo-detector (20) which is coupled to an evaluating unit (22). The imaging device (18) is provided with several different focal lengths which can be selectably brought into the beam path of the overall device. At the start of a measuring process a control device causes the distribution of particle sizes initially to be determined with the use of the longest focal length and employment of evaluation mathematics valid for this focal length. After the evaluating unit (22) has ascertained that particle size fraction into which the largest measured particles fall, another focal length is, if necessary, brought into the beam path of which the measuring range still just reaches over the largest measured particles. Thereupon the apparatus determines the distribution of particle sizes again with the use of the previously selected focal length and evaluation mathematics matched to this, the distance between the photo-detector (20) and the imaging device (18) being matched to the respective focal length disposed in the beam path. Distributions of particle sizes of unknown samples are thus measured with higher resolution and accuracy.

30 Claims, 1 Drawing Sheet

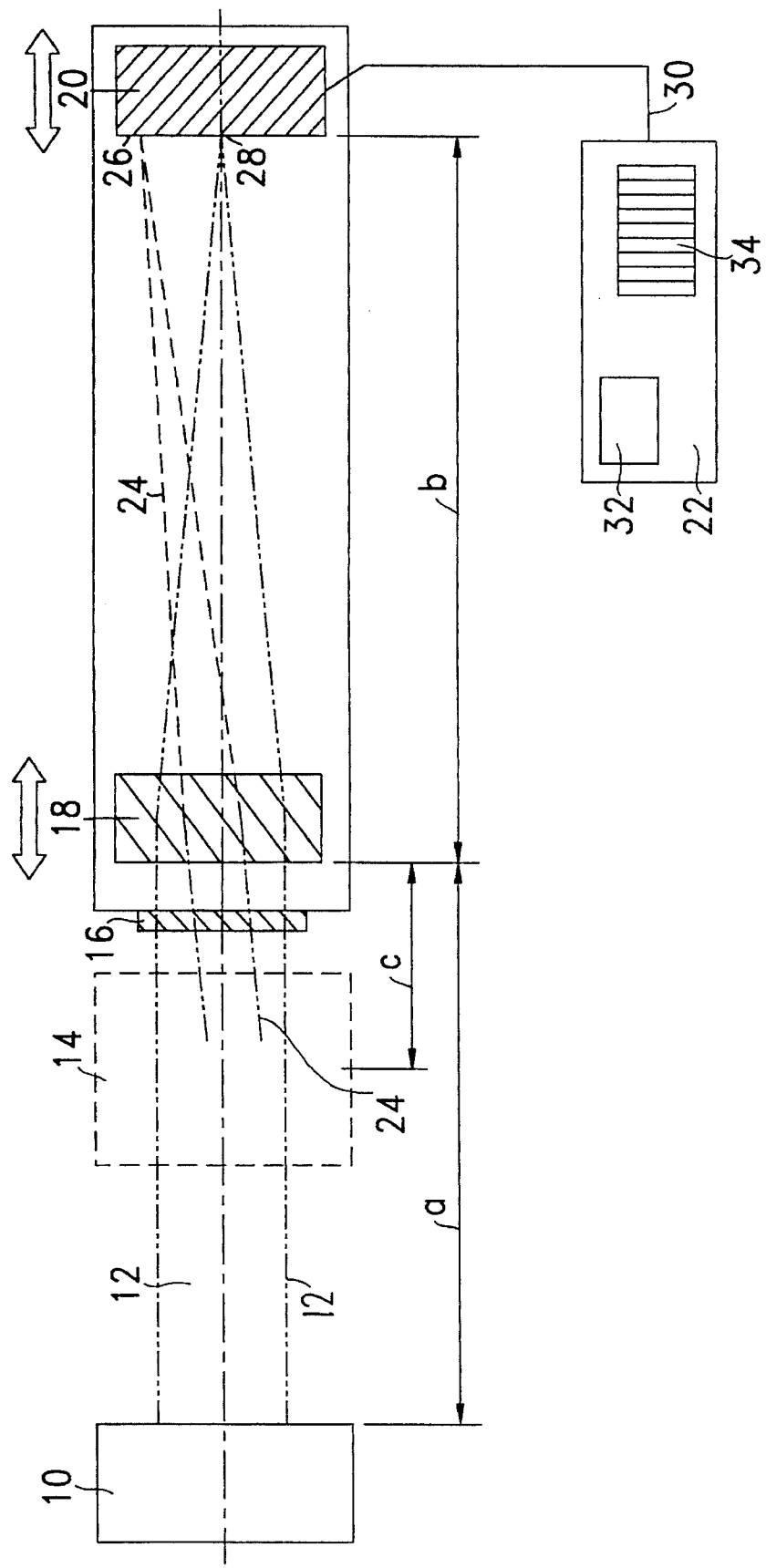

APPARATUS FOR DETERMINATION OF PARTICLE SIZES AND/OR DISTRIBUTIONS OF PARTICLE SIZES

FIELD OF THE INVENTION

The invention relates to apparatus for the determination of particle size data such as particle sizes and/or distribution of particle sizes.

BACKGROUND OF THE INVENTION

Such apparatus is known and has many fields of use for particle size analysis of dispersed substances or drop distributions. In that case use of made of the fact that a particle irradiated by monochromatic light deflects this light to different degrees in dependence on its size, wherein small particles more strongly deflect the light than large particles.

The monochromatic light, usually produced by a laser, is accordingly diffracted by particles which are disposed in a measuring zone. The diffracted light has an angular distribution of intensity which corresponds to the size distribution of the illuminated particles. This angular distribution is converted into a positional distribution by an imaging device in the form of a convergent lens with a focal length f, which intercepts the beam diffracted at the particles, at a spacing therefrom corresponding to the focal length of the convergent lens. This positional distribution is picked up by a photo-detector arranged in the focal plans of this convergent lens and determined by measuring technology by a downstream electronic system. The distribution of the particle sizes is ascertained from the determined intensity distribution by a calculation algorithm (for example, Fraunhofer's Diffraction, Mie Theory). The particles can flow through the measuring zone dry or dispersed as an aerosol in a free jet or they can be dispersed in a liquid which is conducted through a measuring cell arranged in the measuring zone.

Normally, the measuring zone is arranged in the parallel beam path in front of the convergent lens. Then, however, due to the limited area of the conventionally employed photo-detectors only a specific range of particle sizes can be measured in the case of a convergent lens having a predetermined focal length, since, for example, for the measurement of larger particles a convergent lens with a larger focal length is necessary in order to achieve, on the photo detector, an acceptable image of the diffraction pattern which is formed by the beam deflected relatively weakly at the large particles. The large focal length of the lens leads to a correspondingly large housing for the measuring device.

Conversely, for the measurement of very small particle sizes, a lens with a correspondingly small focal length is required, which in addition should still have a largest possible aperture in order to still catch the beam very strongly deflected by the smallest particles. Such lenses having a short focal length inevitably produce, if they are to be affordable, large imaging errors. Accordingly, for the measurement of very small particle sizes it has been proposed (see European patent 0 207 170 B1) to arrange the measuring zone in the convergent beam path between convergent lens and photo-detector. This arrangement is certainly mathematically equivalent, except for a phase factor, to the arrangement in the parallel beam path, but the problem arises that now the distance between the particles and the photo-detector decides the measuring range. This distance cannot be accurately defined, as the guiding of the particles through the measuring zone must be designed for the largest particles to be measured, otherwise an undesired lack of definition in the position inevitably arises in the case of smaller particles flowing through the measuring zone.

In the case of samples with unknown particle size distribution an imaging device with a longer focal length and a correspondingly large measuring range must therefore be used for the determination of the particle size distribution in order to ensure that the largest particles contained in the sample are also detected in the determination. However, in the range of smaller particle sizes the long focal length brings with it a reduced resolution and thus a lower accuracy.

An object of the invention is to provide a device by which unknown distributions of particle sizes can be measured with high resolution in a short time.

SUMMARY OF THE INVENTION

According to one aspect of the invention there is provided apparatus for determination of particle sizes and/or distributions of particle sizes, comprising:

a light source which emits parallel light of high coherence, a measuring zone through which the particles flow and the light is transmitted, an imaging device which images the light beam diffracted at the particles onto a photo-detector arranged in the focal plan of the imaging device, and an evaluating unit, which is connected with the photo-detector, for the ascertaining of particle sizes and/or distributions of particle sizes from the diffraction pattern imaged on the photo-detector.

characterized in that the imaging device is provided with several different focal lengths which can be selectably brought into the beam path, at the start of a measuring process the longest focal length is arranged in the beam path and the distribution of the particle sizes is determined with use of this longest focal length, wherein the evaluating unit employs evaluation mathematics valid for the longest focal length, the evaluating unit ascertains an uppermost particle size fraction into which the largest measured particles fall, in dependence on the ascertain uppermost particle size fraction there is if necessary arranged in the beam path that shorter focal length of which the measuring range still encompasses the uppermost particle size fraction, following thereon a renewed determination of the distribution of particle sizes takes place with use of the focal length now arranged in the beam path, wherein the evaluating unit employs evaluating mathematics matched to the changed measuring range, and the distance between the photo-detector and the imaging device is matched to the respective focal length disposed in the beam path.

Since the imaging device of the apparatus has available several different focal lengths and at the start of a measuring process the distribution of particle sizes is determined by using the longest focal length available, it is initially established which upper particle size fraction is contained in an unknown sample. In accordance with the invention a second complete measuring process is then undertaken with a focal length of which the measuring range just still encompasses the largest ascertained particles. In this manner a considerably higher resolution and accuracy of measurement is achieved with many samples without the expenditure of a substantial increase in time. The evaluation mathematics employed for ascertaining the particle size distribution and known per se (see, for example, B. M. Heuer, lecture at the 3rd symposium "Granulometrie", Dresden, 15 Dec. 1983) are automatically matched to the measuring range changed with the focal length. The distance between the photo-detector receiving the diffraction pattern and the imaging device is similarly matched to the respective focal length disposed in the beam path, so that a maximum of accuracy is guaranteed. This matching is preferably effected automatically for reduction in operating effort.

According to another aspect of the invention there is provided apparatus for determination of particle sizes and/or distributions of particle sizes, comprising a light source which emits parallel light of high coherence, a measuring zone through which the particles flow and the light is transmitted, an imaging device which images the light beam diffracted at the particles onto a photo-detector arranged in the focal plane of the imaging device, and an evaluating unit, which is connected with the photo-detector, for the ascertaining of particle sizes and/or distribution of particle sizes from the diffraction pattern imaged on the photo-detector, characterized in that the imaging device is provided with several different focal lengths which can be selectably brought into the beam path, at the start of a measuring process a first focal length is arranged in the beam path and the distribution of the particle sizes is determined with use of this first focal length, wherein the evaluating unit employs evaluation mathematics valid for this first focal length, the evaluating unit ascertains whether the uppermost particle size fraction of the measuring range encompassed by the first focal length is occupied, if the uppermost particle fraction of the measuring range of the first focal length is not occupied, an available longer focal length with correspondingly larger measuring range is then arranged in the beam path and following thereon a renewed determination of the distribution of particle sizes takes place with use of the focal length now arranged in the beam path, wherein the evaluating unit employs evaluating mathematics matched to the changed measuring range, if the uppermost particle size fraction of the measuring range of the first focal length is not occupied, the evaluating unit then ascertains that particle size fraction in which the largest measured particles fall and in dependence on the thus detected particle size fraction there is arranged in the beam path that available shorter focal length of which the measuring range still encompasses the previously ascertained particle size fraction, whereupon a renewed determination of the distribution of particle sizes takes place with use of the focal length now arranged in the beam path, wherein the evaluating unit employs evaluating mathematics matched to the changed measuring range, and the distance between the photo-detector and the imaging device is matched to the respective focal length disposed in the beam path.

The difference from the above-described apparatus consists in that the measuring of the particle size distribution is not necessarily begun with the longest available focal length, but with any one of the available focal lengths, for example that which is still disposed in the beam path from a previous measuring process. In this embodiment the evaluating unit initially ascertains whether the uppermost particle size fraction of the measuring range, which is encompassed by the first focal length disposed in the beam path, is occupied. If this is the case, a longer focal length—insofar as present is arranged in the beam path and a measuring of the particle size distribution is performed again. This process is, if necessary, repeated until there is disposed in the beam path of the apparatus a focal length which encompasses a measuring range in which all the particle sizes of a sample to be tested can be detected. If, however, the uppermost particle size fraction of the measuring range encompassed by the first focal length is not occupied, then analogously to the first embodiment that particle size fraction is ascertained in which the largest measured particles fall. Insofar as present, there is then arranged in the beam path that shorter focal length of which the measuring range still encompasses the ascertained particle size fraction and subsequently a renewed determination of the particle size distribution is performed.

In both embodiments a control means preferably provides an automatic selection and arrangement of the focal lengths in the beam path, wherein the control means at the same time also automatically adapts the spacing between the photo-detector and the imaging device to the respective focal length disposed in the beam path.

In a preferred embodiment of the apparatus according to the invention at least one focal length of the imaging device is formed by a multi-lens optical systems. In the case of long focal lengths this has the advantage that, in contrast to the single lens conventionally used, the length of the housing of the apparatus no longer lies in the order of magnitude of the focal length, but can be considerably shorter. Apart from an earlier handling capability the shorter housing length also leads to more accurate measuring results, as not only stresses and torsions of the optical bench, on which the principal components are secured in conventional apparatus of this kind, but also local changes, caused by temperature fluctuations, of the refractive index (striation) of the air disposed between imaging device and photo-detector, increase more than proportionally with increasing length. A further advantage of the construction of a long focal length as a multi-lens optical system results from the possibility of enlarging the entry opening of the imaging device, i.e. the opening of the imaging device facing the measuring zone, and thereby being able to increase the distance between measuring zone and imaging device. Thus, for example, the distance between measuring zone and imaging device in the case of a focal length of 2,000 mm can be more than 1,800 mm and in the case of a focal length of 1,000 mm can be more than 900 mm. These large, previously unattainable, spacings to the measuring zone are indispensable if the imaging device cannot be arranged close enough to the measuring zone and measuring was accordingly hitherto not possible, for example if the measuring zone is disposed behind a glass pane.

With short focal lengths, the previously problematic very small distance between imaging device and photo-detector can be increased to a practicable dimension through the use of a multi-lens optical system. Moreover, compared to a single lens of short focal length, the lens errors of the multi-lens optical system are greatly reduced. The use of multi-lens optical systems of short focal length additionally opens up the possibility of carrying out measurements in the submicron range in the parallel beam path. In order, in the case of a variable distance between measuring zone and imaging device, to catch as fully as possible the beam diffracted at the submicron particles the aperture of the imaging device must be very large. These large apertures are only achievable with multi-lens optical systems. Single lenses with the apertures necessary for this range are not available.

In general, in the case of use of a multi-lens optical system the constructional length of the measuring is not necessarily coupled with the particle size to be measured. An effective focal length of 1,000 mm can, for example, be achieved by a convergent lens, functioning as an entry lens, having a focal length of 200 mm and a divergent lens, functioning as an exit lens, having a focal length of minus 70 mm, whereby the distance between the imaging device and the photo-detector reduces by 1,000 mm to about 400 mm.

Thus, even very small particles dispersed drying the free jet and aerosols can be measured in the parallel beam path, which hitherto was substantially impossible or at least very difficult.

A preferred device according to the invention comprises an imaging device with focal lengths of 20 mm, 50 mm, 100 mm, 200 mm, 500 mm, 1,000 mm and 2,000 mm. A particle size range of about 0.1 microns to 3,500 microns can be measured with high resolution with these focal lengths.

In a particularly preferred device according to the invention the imaging device additionally has focal lengths of 10 mm and/or 5,000 mm, so that particles of less than 0.1 micron size and/or up to 8,750 micron size can be measured with high resolution.

The aforementioned stepping of the focal lengths of the imaging device obtains the so-called pitch of the measuring device and thereby facilitates the comparability of measurement results obtained by the apparatus according to the invention with measurement results of other apparatus of which the support points used in the evaluation are the same.

In order to be able to fully utilize the above-described advantages resulting from the employment of different focal lengths and the use of multi-lens optical systems, the distance between the measuring zone and the imaging device is advantageously adjustable. Preferably, this embodiment comprises a narrow-band interference filter arranged in the beam path in front of the imaging device in order to reduce the influence of interference light, which in the case of a variable spacing between measuring zone and imaging device could pass with amplification into the housing and to the photo-detector. Preferably the interference filter is arranged in the beam path directly in front of the imaging device and has a transmission maximum which corresponds to the fundamental wavelength of the light emitted by the light source. The ratio of usable light intensity to interference light is thus better than 100:1.

In one embodiment of the apparatus according to the invention the distance between the photo-detector and the imaging device is controllable in that the photo-detector is moved by a spindle drive, which is connected with the control means, into a position which is synchronized with the respective focal length disposed in the beam path.

In all embodiment of the apparatus according to the invention the light source is preferably a laser and the photo-detector is preferably of multi-element type.

DESCRIPTION OF A PREFERRED EMBODIMENT

One embodiment of apparatus according to the invention is explained in more detail with reference to the accompanying schematic drawing.

The single FIGURE shows an apparatus for the determination of particle sizes and/or distributions of particle sizes, comprising an instrument head 10 for generating a parallel laser beam 12, a measuring zone 14, a narrow-band interference filter 16, an imaging device 18, a multi-element photo-detector 20 and an electronic evaluating unit 22.

The laser beam 12 passes through the measuring zone 14 which is arranged substantially normal thereto and in which the particles to be measured are disposed. The measuring zone 14 can consist of a free jet, in which the particles are dispersed dry or as an aerosol, or it can be formed by a measuring cell in which the particles are dispersed in a fluid.

Laser rays 24 diffracted at the particles disposed in the measuring zone 14 enter, together with the non-diffracted laser ray 12, into the imaging device 18 after they have passed the interference filter 16 serving for the diminution of interference light. The distance, designated by a, between the instrument head 10 and the imaging device 18 is physically limited only by the fact that the diffracted rays 24 must pass into the entry opening of the imaging device 18.

The imaging device 18 images the diffracted and the non-diffracted rays on the photo-detector 20 arranged at a spacing b from the imaging device. The distance b between imaging device 18 and photo-detector 20 depends on the focal length of the imaging device 18, but is not necessarily identical therewith. The position of the focused rays on the photo-detector 20 varies according to the respective angle of entry of the diffracted rays 24 into the imaging device. In the illustrated example the diffracted rays 24 are focused at a position designated by 26, and the non-diffracted laser ray 12 is focused at a point designated by 28, on the photo-detector 20.

The intensity distribution of the laser light, which is given by the diffraction pattern imaged on the photo-detector 20, is resolved by the individual elements of the photo-detector 20 and corresponding signals are conducted by way of the line 30 to the evaluating unit 22 which ascertains therefrom the particle sizes as well as the size distribution thereof by utilizing a calculation algorithm.

The imaging device 18 has not one, but seven different focal lengths, which can be selectively arranged in the beam path. In that case focal lengths of 100 mm, 200 mm and 500 mm are realized as single lens, while multi-element optical systems come into use for focal lengths of 20 mm, 50 mm, 1,000 mm and 2,000 mm. Depending upon the focal length, which is disposed in the beam path of the imaging device 18 the photo-detector 20 is moved by a setting motor (not shown) and a spindle drive into a position which is associated with the corresponding focal length and which was ascertained to be the optimal position for this focal length.

In order to able to adapt the measuring apparatus to different requirements, the distance c between the measuring zone 14 and the imaging device 18 is similarly adjustable.

An automated operational sequence of the illustrated measuring apparatus is described in more detail below:

It will be assumed that a plurality of particles of unknown sizes is disposed in the measuring zone 14. After the measuring apparatus has been activated by a not-illustrated control which is either integrated in the evaluating unit 22 or separate, the largest measuring range is automatically set, i.e. the imaging device is automatically selects the longest focal length, which in the example of the embodiment described here is 2,000 mm and encompasses a measuring range of 0.1 microns to 3,500 microns, in the beam path. Substantially simultaneously the setting motor of the spindle drive is driven and moves the photo-detector 20 into the position associated with the longest focal length.

A first measuring process now takes place similarly automatically. The evaluating unit 22 ascertains the particle size distribution with the use of evaluation mathematics (set of equations) valid for the longest focal length or the largest measuring range. Insofar as finer particles are concerned, the upper particle size fractions provided for particles of larger diameter are not occupied (see Table 1).

The evaluating unit 22 ascertains in the next step the uppermost occupied particle size fraction, that is the fraction into which the largest particles present in the sample fall.

According to Table 1, the uppermost occupied particle size fraction in this case is that with an upper limit of 720 microns. Consequently, the control selects, for example, a focal length of the imaging device 18, in which the uppermost occupied particle size fraction is just still contained within the measuring range, in that it compares the uppermost occupied particle size fraction with the list of measuring ranges shown in Table 2. In the described example there thus results from Table 2 a focal length of 500 mm, the measuring range of which extends to 875 microns. The imaging device, activated by the control, then automatically moves this focal length into the beam path. At approximately the same time the photo-detector 20 also moves into the position associated with the selected focal width. The evaluation mathematics are changed over in the evaluating unit 22 to the measuring range now disposed in the beam path. Subsequently, a further measuring process and calculation of the particle size distribution takes place with use of these evaluation mathematics. As a final step the result is either displayed on a screen 32 of the evaluating unit 22 or printed out by a printer (not shown) connected with the latter. A keyboard for operation of the evaluating unit 22 is designated by 34.

TABLE 1

Measurement of particles dispersed dry in a free jet, with a focal length f = 2,000 mm

| Upper Particle Size Fraction in microns | Logarithmic Density $q^3{}_{lg}$ |
|---|---|
| 18.00 | 4.84 |
| 22.00 | 9.29 |
| 26.00 | 10.77 |
| 30.00 | 12.25 |
| 36.00 | 14.12 |
| 44.00 | 16.77 |
| 52.00 | 19.83 |
| 62.00 | 23.32 |
| 74.00 | 27.66 |
| 85.00 | 32.35 |
| 100.00 | 37.29 |
| 120.00 | 43.24 |
| 150.00 | 50.69 |
| 180.00 | 56.63 |
| 210.00 | 56.48 |
| 250.00 | 48.10 |
| 300.00 | 32.87 |
| 360.00 | 17.27 |
| 420.00 | 6.36 |
| 500.00 | 1.05 |
| 600.00 | 0.72 |
| 720.00 | 2.15 |

TABLE 1-continued

Measurement of particles dispersed dry in a free jet, with a focal length f = 2,000 mm

| Upper Particle Size Fraction in microns | Logarithmic Density $q^3{}_{lg}$ |
|---|---|
| 860.00 | 0.00 |
| 1,020.00 | 0.00 |
| 1,220.00 | 0.00 |
| 1,460.00 | 0.00 |
| 1,740.00 | 0.00 |
| 2,060.00 | 0.00 |
| 2,460.00 | 0.00 |
| 2,940.00 | 0.00 |
| 3,500.00 | 0.00 |

TABLE 2

| Focal Length | Particle Size Range |
|---|---|
| 20 mm | 0.1 microns–35 microns |
| 50 mm | 0.25 microns–87.5 microns |
| 100 mm | 0.5 microns–175 microns |
| 200 mm | 0.5 microns–350 microns |
| 500 mm | 0.5 microns–875 microns |
| 1,000 mm | 0.5 microns–1750 microns |
| 2,000 mm | 0.5 microns–3500 microns |

As is apparent from the foregoing description of the operation sequence, the measuring and determination of the particle size distribution takes place fully automatically after the activation of the device. In this manner an even higher accuracy is achieved by comparison with manually operated apparatus, as movements in the proximity of the measuring zone, which can lead to errors particularly in the case of dry measuring, and the opening of the housing for changing the focal length of the imaging device 18 and of the position of the photo-detector, which can lead to light vibration of housing components after the closure of the housing, cannot occur.

We claim:

1. An apparatus for determining a size distribution of particles comprising:

a) a source providing a high-coherence parallel light beam directed through a measuring zone, the measuring zone including the particles;

b) an imaging device for imaging a pattern of light, diffracted by the particles of the measuring zone, the imaging device having a focal plane and selectively disposing at least one of a plurality of focal lengths into a path of the light beam, each focal length having a corresponding measuring range, a longest of the plurality of focal lengths being first disposed in the path of the light, and selectively disposing a shorter focal length into the path of the light upon a determination of an uppermost particle size fraction and based on the determination;

c) a photo-detector disposed in the focal plane of the imaging device to receive the pattern of diffracted light imaged by the imaging device, and being adjusted such that a distance between the photo-detector and the imaging device is based on the focal length being selectively disposed in the path of the light beam; and d) an evaluating unit coupled with the photo-detector and employing a plurality of calculation algorithms corresponding to, and valid for, the plurality of focal lengths, the evaluating unit first employing a calculation algorithm corresponding to, and valid for, the longest focal length, the evaluating unit ascertaining which uppermost particle size fraction is occupied by the particles based on the pattern of light imaged by the imaging device and received by the photo detector, determining and selecting the shortest of the plurality of focal lengths having a measuring range encompassing the uppermost particle size fraction, adjusting the position of the photo-detector relative to the imaging device based on the selected focal length, and employing a calculation algorithm corresponding to the measuring range associated with the selected focal length wherein a longest of the plurality of focal lengths is first arranged in the light path, and the evaluating unit employs evaluation mathematics valid for the longest focal length to ascertain whether an uppermost particle size fraction is occupied, selects dependent upon whether the ascertained uppermost particle size fraction is occupied a shorter focal length of which a measuring range corresponding to the focal length encompasses the uppermost particle size fraction, selects and employs a calculation algorithm corresponding to the measuring range associated with the selected shorter focal length, and adjusts the distance between the photo-detector and the imaging device to determine the particle size distribution.

2. The apparatus according to claim 1, further comprising a controller for automatically and selectively disposing the respective focal length in the light beam path and being coupled to the evaluating unit.

3. The apparatus according to claim 1, further comprising a controller for automatically controlling the distance between the photo-detector and the imaging device and being coupled to the evaluating unit.

4. The apparatus according to claim 1, wherein at least one focal length of the imaging means is formed by a multi-lens optical system.

5. The apparatus according to claim 1, wherein a distance between the measuring zone and the imaging means is adjustable.

6. The apparatus according to claim 1, further comprising a narrow-band interference filter disposed in the light beam path between the measuring zone and the imaging means.

7. The apparatus according to claim 6, wherein the interference filter is arranged in the light beam path directly in front of the imaging means and has a transmission maximum which corresponds to a main wavelength of the light emitted by the light source.

8. The apparatus according to claim 1, wherein the imaging device is provided with focal lengths of 20 mm, 50 mm, 100 mm, 200 mm, 500 mm, 1,000 mm and 2,000 mm.

9. The apparatus according to claim 1, wherein the imaging device is provided with a focal length of 10 mm.

10. The apparatus according to claim 1, wherein the imaging device is provided with a focal length of 5,000 mm.

11. The apparatus according to claim 1, wherein the light source is a laser.

12. The apparatus according to claim 1, wherein the photo-detector is a multi-element photo-detector.

13. The apparatus according to claim 1, further comprising: a setting motor; and a spindle drive coupled with the setting motor wherein the setting drive and the spindle motor move the photo-detector into a position appropriate to the respective focal length disposed in the light beam path.

14. The apparatus according to claim 1, wherein characteristic particle sizes range from less than 0.1 microns up to 8.750 microns are resolved.

15. An apparatus for determining particle size comprising:

a) a source of high-coherence parallel light comprising a beam directed through a measuring zone arranged such that the light beam may be transmitted therethrough, and such that particles may also pass therethrough;

b) an imaging device for imaging a pattern of light diffracted by the particles passing in the measuring zone through the high-coherence parallel light, the imaging device having a focal plane and a plurality of focal lengths that can be selectively disposed into a path of the light beam, each focal length having a corresponding measuring range, and one of the plurality of focal lengths being first disposed in the path of the light, and other longer or shorter focal lengths being selectably disposable in the path of the light upon a determination of an uppermost particle size;

c) a photo-detector disposed in the focal plane of the imaging device to receive the image of the diffraction pattern, and capable of being adjusted such that the distance of the photo-detector from the imaging device relates to a respective focal length of the plurality of focal lengths; and d) an evaluating unit coupled to the photo-detector and employing a plurality of calculation algorithms corresponding to and valid for the plurality of focal lengths, the evaluating unit first employing a calculation algorithm corresponding to and valid for the focal length first disposed in the path of the light, the evaluating unit furthermore capable of ascertaining from the diffraction pattern which uppermost particle size fraction of a measuring range corresponding to the first disposed focal length is occupied and, if it is, selecting a longer available focal length and disposing it into the light beam path, adjusting the position of the photo-detector to based algorithm selected focal length, and employing a calculation algorithm corresponding to the measuring range associated with the selected focal length; and furthermore capable, if the uppermost particle size fraction is not occupied, of selecting a shorter available focal length corresponding to the largest measured particle size and disposing the selected focal length into the light beam path, adjusting the position of the photo-detector based on the selected focal length and employing a calculation algorithm corresponding to the measuring range associated with the selected focal length;

wherein one of the plurality of focal lengths is first arranged in the light path and the evaluating unit employs a calculation algorithm valid for the longest focal length to ascertain whether an uppermost particle size fraction is occupied, selects dependent upon whether the ascertained uppermost particle size fraction is occupied a longer focal length, employs a calculation algorithm corresponding to the measuring range associated with the selected shorter focal length, disposes it into the light beam path, and adjusts the distance between the photo-detector and the imaging device based on the longer focal length; but, if the ascertained uppermost particle size fraction is not occupied, selects a shorter focal length corresponding to the largest measured particle size, disposes it into the light beam path, employs a calculation algorithm corresponding to the measuring range associated with the selected shorter focal length, and adjusts the distance between the photo-detector and the imaging device based on the shorter focal length to determine the particle size distribution.

16. The apparatus according to claim 15, further comprising a controller for automatically and selectively disposing the respective focal length in the light beam path and being coupled to the evaluating unit.

17. The apparatus according to claim 15, further comprising a controller for automatically controlling a distance between the photodetector and the imaging device and being coupled to the evaluating unit.

18. The apparatus according to claim 15, wherein at least one focal length of the imaging means is formed by a multi-lens optical system.

19. The apparatus according to claim 15, wherein a distance between the measuring zone and the imaging means is adjustable.

20. The apparatus according to claim 15, further comprising a narrow-band interference filter disposed in the light beam path between the measuring zone and the imaging means.

21. The apparatus according to claim 20, wherein the interference filter is arranged in the beam path directly in front of the imaging means and has a transmission maximum which corresponds to a main wavelength of the light emitted by the light source.

22. The apparatus according to claim 15, wherein the imaging device is provided with focal lengths of 20 mm, 50 mm, 100 mm, 200 mm, 500 mm, 1,000 mm and 2,000 mm.

23. The apparatus according to claim 15, wherein the imaging device is provided with a focal length of 10 mm.

24. The apparatus according to claim 15, wherein the imaging device is provided with a focal length of 5,000 mm.

25. The apparatus according to claim 15, wherein the light source is a laser.

26. The apparatus according to claim 15, wherein the photo-detector is a multi-element photo-detector.

27. The apparatus according to claim 15, further comprising: a setting motor; and a spindle drive coupled with the setting motor, the setting motor and the spindle drive moving the photo-detector into a position appropriate to the respective focal length disposed in the beam path.

28. The apparatus according to claim 15, wherein characteristic particle sizes ranging from less than 0.1 microns up to 8.750 microns are resolved.

29. In an apparatus for determining a size distribution of particles having a source of a high-coherence parallel light beam, the light beam directed through a measuring zone including the particles; an imaging device for imaging a pattern of light diffracted by the particles passing through the high-coherence parallel light, having a focal plane and a plurality of focal lengths; a photo-detector disposed in the focal plane of the imaging device to receive the image of the diffraction pattern; and an evaluating unit coupled to the photo-detector and employing a plurality of calculation algorithms corresponding to, and valid for, the plurality of focal lengths, a method for determining particle size comprising the steps of:

a) disposing the longest focal length of the plurality of focal lengths in the beam path such that the light beam diffracted by particles in the measuring zone passes through the imaging device and is received by the photo-detector as a diffraction pattern;

b) determining with the evaluating unit which employs a calculation algorithm corresponding to, and valid for, the longest focal length, an uppermost particle size fraction based on the diffraction pattern received by the photo-detector;

c) selecting and disposing in the light beam path a shortest focal length having a range including the uppermost particle size fraction;

d) selecting a calculation algorithm corresponding to, and valid for, the shorter focal length for employment by the evaluation unit; and e) adjusting a distance between the photo-detector and the imaging device based on the focal length disposed in the beam path.

30. In an apparatus for determining a size distribution of particles having a source of a high-coherence parallel light beam, the light beam directed through a measuring zone including the particles; an imaging device for imaging a pattern of light diffracted by the particles passing through the high-coherence parallel light, having a focal plane and a plurality of focal lengths; a photo-detector disposed in the focal plane of the imaging device to receive the image of the diffraction pattern; and an evaluating unit coupled to the photo-detector and employing a plurality of calculation algorithms corresponding to, and valid for, the plurality of focal lengths, a method for determining particle size comprising the steps of:

a) disposing a first focal length of the plurality of focal lengths in the beam path such that the light beam diffracted by particles in the measuring zone passes through the imaging device and is received by the photo-detector as a diffraction pattern;

b) determining with the evaluating unit which employs a calculation algorithm corresponding to and valid for the longest focal length, whether an uppermost particle size fraction associated with the first focal length is occupied, based on the diffraction pattern received by the photo-detector;

c) if the uppermost particle size fraction is occupied:
  1. selecting and disposing in the beam path a longer focal length than the first focal length;
  2. selecting a calculation algorithm corresponding to, and valid for, the longer focal length for employment by the evaluation unit; and
  3. adjusting a distance between the photo-detector and the imaging device based on the longer focal length disposed in the beam path; and d) if the uppermost particle size fraction is not occupied:
  1. determining, with the evaluating unit which employs a calculation algorithm corresponding to, and valid for, the first focal length, an uppermost particle size fraction based on the diffraction pattern received by the photo-detector;
  2. selecting and disposing in the beam path a shortest focal length having a measuring range including the determined uppermost particle size fraction;
  3. selecting a calculation algorithm corresponding to, and valid for, the shortest focal length for employment by the evaluation unit; and
  4. adjusting a distance between the photo-detector and the imaging device based on the shortest focal length disposed in the beam path.

* * * * *